(12) United States Patent
Schultz

(10) Patent No.: US 6,705,862 B2
(45) Date of Patent: Mar. 16, 2004

(54) ADVANCED BUCCAL TUBE

(75) Inventor: Charles J. Schultz, West Babylon, NY (US)

(73) Assignee: Dentsply Research & Development Corp.

(*) Notice: Subject to any disclaimer, the term of this patent is extended or adjusted under 35 U.S.C. 154(b) by 153 days.

(21) Appl. No.: 10/109,124

(22) Filed: Mar. 27, 2002

(65) Prior Publication Data

US 2003/0186185 A1 Oct. 2, 2003

(51) Int. Cl.[7] .................................................. A61C 3/00
(52) U.S. Cl. ........................................................ 433/17
(58) Field of Search .............................. 433/10, 13, 17

(56) References Cited

U.S. PATENT DOCUMENTS

| | | |
|---|---|---|
| 3,391,461 A | 7/1968 | Johnson |
| 3,874,080 A | 4/1975 | Wallshein ................. 32/14 |
| 4,669,797 A | 6/1987 | Bourdon ................... 433/4 |
| 4,927,362 A | 5/1990 | Snead ...................... 433/17 |
| 4,963,092 A | 10/1990 | Snead ...................... 433/17 |
| 5,057,012 A | 10/1991 | Kesling .................... 433/17 |
| 5,059,119 A | 10/1991 | Snead ...................... 433/17 |
| 5,151,028 A | 9/1992 | Snead ...................... 433/17 |
| 5,288,229 A | 2/1994 | Huff et al. ............... 433/17 |
| 5,292,248 A | 3/1994 | Schultz .................... 433/17 |
| 5,556,277 A | 9/1996 | Yawata et al. ........... 433/17 |
| 5,910,007 A * | 6/1999 | Shimodaira et al. .... 433/17 |
| 6,428,314 B1 | 8/2002 | Jones, Jr. et al. ....... 433/17 |

* cited by examiner

Primary Examiner—Todd E. Manahan
(74) Attorney, Agent, or Firm—James B. Bieber

(57) ABSTRACT

A convertible buccal tube is disclosed which includes an arch wire slot covered by a separable cover. The cover includes a mesial or front flared portion to facilitate placing the end of an arch wire therein without undesirably stressing the cover. The cover is further secured to the buccal tube body by integral seams, brazing or other adhesive means that are varied in strength mesially-distally, with about 50% greater force being required to separate the cover at the mesial end thereof. The cover and increased strength seams provide that the cover is not prematurely separated from the buccal tube, particularly during installation of an arch wire.

16 Claims, 2 Drawing Sheets

ADVANCED BUCCAL TUBE

FIELD OF INVENTION

The invention is directed to orthodontic buccal tubes for securing an arch wire to a tooth. More particularly, the invention is directed to those buccal tubes including a separable cover or cap over an arch wire slot such that the buccal tube may be converted to function as a conventional bracket with an open slot.

BACKGROUND OF THE INVENTION

Orthodontists often employ on first molars buccal tubes that include a convertible or removable cap or cover to facilitate engaging an arch wire initially. When a second molar is then subsequently to be engaged, the first molar tube cover is removed and the terminal of a new arch wire is extended into a new buccal tube mounted on the second molar, with the first buccal tube then functioning as a conventional bracket with an open arch wire slot.

Use of the convertible buccal tubes is not without difficulty. Placing the arch wire into such a tube can be challenging when a tooth is rotated or canted in relationship to the adjoining bicuspid. The convertible cap may require expensive brazing to the tube body and brazing materials may pose biocompatibility problems, unless the design and materials are carefully selected. A major difficulty has been ensuring that the cap does not separate prematurely. Such premature separation may significantly disrupt an orthodontic treatment plan or require expensive remedial work.

Premature separation is particularly a risk when an arch wire is initially fed into the tube. As noted above, placing the arch wire is difficult and may result in excessive forces being asserted. One prior design flares the mesial entryway to a solid tube to allow greater access to start the wire. This design, however, makes feeding the wire from the first to a second molar, more difficult as the enlarged first molar blinds the operator to the second molar tube. Also, due to its high buccal profile, the prior art buccal tube is uncomfortable for the patient when second molars are erupted U.S. Pat. No. 4,927,362 secures a convertible cap to an arch wire slot by employing frangible webs along the length of the buccal tube that are sintered into the tube during manufacture. This system provides some reliability, through uniformity of web thicknesses, in resisting premature separation at reasonable manufacturing cost. However, U.S. '362 does not address the difficulty of inserting large cross sectional wires early in treatment. This issue has become critical with new advanced archwires having superelastic qualities that are increasingly being used by professionals. These wires are flexible and respond to low forces but are characterized by large cross sections.

It is evident that the forces applied by users are much higher at the mesial end than at the distal end of the buccal tube. This is related to the difficulty of large wire insertion that tends to exert higher pressures at the entryway or mesial portion of the cover than at its distal portion. The prior art including US '362 which employs a uniform web mesially-distally, has failed to adequately secure the convertible cover to the tube body such that premature separation of the cover remains a risk due to those higher mesial forces.

SUMMARY

An object of the present invention is to solve the difficulties encountered in employing convertible buccal tubes and to provide a convertible buccal tube having a cover over an arch wire slot that does not prematurely separate.

The invention provides a convertible buccal tube wherein an arch wire slot cover is designed to resist premature separation from the body when subjected to forces that otherwise would cause separation during normal utilization, particularly when an arch wire is initially inserted into the tube arch wire slot.

The convertible buccal tube in a first embodiment of the invention comprises a base attachable to a tooth surface or band on a tooth. The buccal tube further comprises a body fixed to or integral with the base, projecting from the base to define a mesially-distally extending arch wire slot. A cover extends over the slot including mesial-distal seams that are integral between the cover and the body and of a strength selected to facilitate disengaging of the cover from the body but only when an intentional separating force is exerted thereon. The integral seams of the invention are designed and dimensioned to be stronger at their mesial portions than their distal portions such that a larger force must be exerted on the mesial position to initiate disengagement of the cover than required for the distal portion.

A second embodiment of the invention comprises a mesially-distally extending arch wire slot and a convertible cover or cap extending over the slot, wherein the cover is adhered or brazed to the top of the slot using a larger amount of bonding material mesially such that a significantly larger force must be used to disengage the mesial portion of the cover than its distal portion, thus reducing the risk of accidental disengagement. In a preferred design the top of the arch wire slot is provided with parallel mesial-distal extending ledges to accommodate said cap, both ledges and the corresponding cap contact surfaces being mesially-distally tapered, wherein, for example, 50% more bonding material, such as solder, secures the cap to the slot mesially then distally.

Additionally, the convertible cover includes a flared mesial portion such that the covered arch wire slot has a greater opening at its mesial portion than the distal portion which facilitates engagement at the arch wire slot by an arch wire while avoiding the arch wire exerting incidental separating forces on the cover during fitting of an arch wire into a buccal tube arch wire slot.

Preferably, the cover and arch wire slot are formed with integral seams or bonding surfaces that taper mesially-distally wherein the force required to separate the cover is 50% greater at its mesial end than the separation force selected for the distal end of the cover. The flared portion of the cover preferably provides a 50% greater cross-sectional area at the entryway to the arch wire slot. The flared portion is extended only about 25% of the length of the arch wire slot whereby the remaining portion of the combination cover and arch wire slot secure the arch wire in position.

DESCRIPTION OF THE PREFERRED EMBODIMENTS

Figure 1:
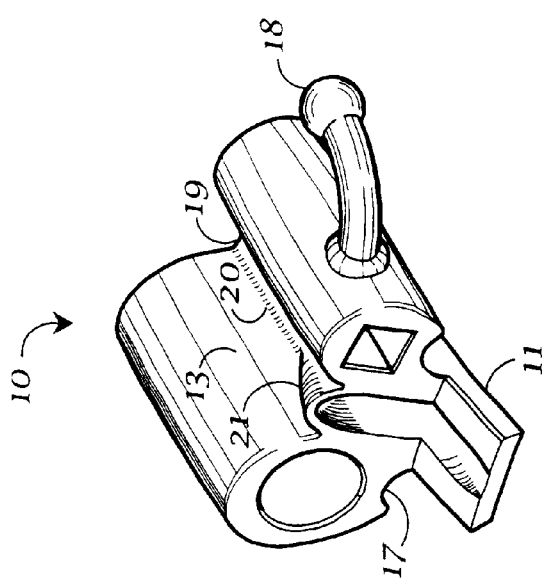
FIG. 1 is a perspective view of an embodiment of an orthodontic convertible buccal tube of the invention.
Figure 2:
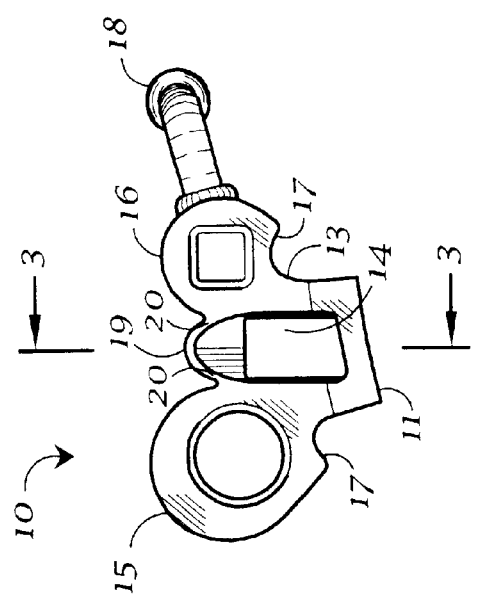
FIG. 2 is a front mesial or front elevational view of the buccal tube of FIG. 1.

Referring to FIGS. 1 and 2, an embodiment 10 of the convertible buccal tube of the invention is shown. The buccal tube 10 of the invention includes a base 11 for attaching to a tooth or molar band (not shown). A body 13 extends from base 11 defining an arch wire slot 14. The body 13 may also include fittings for other accessories such as a head gear tube 15 and an auxiliary tube 16. The body 13 also defines the wings 17. The body 13 may also support other attachment accessories such as a ball hook 18. The arch wire slot 14 extends mesial-distally and is typically of a rectangular cross section to receive an arch wire (not shown). The buccal tube 10 of the invention includes a cap or convertible cover 19 which extends mesially-distally, covering the arch wire slot 14. The cover 19 is secured to the tube body 13 by means of parallel seams 20 that are integrally formed with the tube body 13.

In use, the convertible buccal tube base 11 of the invention is secured to a first molar tooth. A terminal end of an arch wire is inserted into the tube and its end secured thereto, wherein the tooth/buccal tube anchors the dental arch for that wire. After the patient's second molar erupts, a new buccal tube is installed on the molar to serve as the terminal anchor. The convertible cover or cap 19 is separated to convert the tube on the first molar into an edgewise bracket with a buccally open arch wire slot and a new arch wire secured to the new buccal tube on the second molar.

A key feature of the invention is that the convertible cover 19 is designed to resist premature separation from the tube body when subjected to forces that otherwise would cause separation during normal utilization, particularly during initial insertion of an arch wire in the tube slot 14. The new design provides two improved design aspects: (1) a cover having a flared mesial entryway; and (2) a cover being secured to the body such that an increased force is required to separate the cover, but preferably only at its front (mesial) end.

Figure 3:
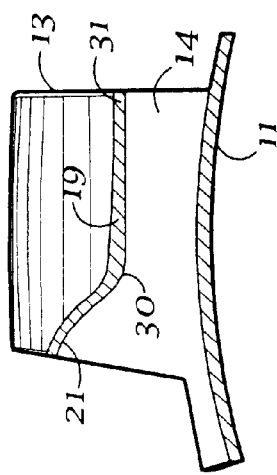
FIG. 3 is a cross sectional view of FIG. 1, taken along lines 3—3.

Referring to FIGS. 1–3, the cap 19 includes a mesial flare or ramp 21, best shown in section in FIG. 3. Preferably, the mesial flare extends for at least an initial portion of the cover. Most preferably the mesial flare extends for the first 0.5 mm of the cap 19 and then ramps down to the typical desired slot specification at 1–1.5 mm. The ramp 21 is intended to help guide an arch wire into the slot (14), facilitating easier arch wire insertion and reducing the tendency of excessive stresses to be exerted on the cap 19 in trying to engage the wire. The ramp also protects or cushions the soft tissue abutting the flared entryway from inadvertent contact with the arch wire.

Preferably the cover flare or ramp 21 will flare out about 50% larger than the conventional arch wire slot. The flare 21 may extend for preferably 1 mm of the overall typical mesial distal length of 4 mm, reducing to the conventional arch slot 14 dimensions to secure the arch wire in place.

A second noted key aspect of the invention is that the integral seams 20 are engineered such that the risk of premature separation is reduced. The integral seams are designed such that a greater force is required at the mesial dimension 30 to initiate separation, since it has been observed that the mesial front portion of the buccal tubes is often subjected to the greatest and sometimes excessive pressure that causes undesired separations.

Preferably, the minimum seam dimensions 31 are selected for an overall separation force of on the order of 10 kg that will generally be sufficient to maintain the cover in position under normal operations while permitting removal with reasonable effort. To reduce premature separation the mesial front portion 30 of the integral seams are dimensioned to separate at about 15 kg of force, significantly reducing premature separations. The preferred separation forces may be provided by, for example, tapering the thickness of the cap and integral seams from a mesial dimension 30 to the distal end dimension 31. That is, the seams 20 at the cover entryway are thicker than the distal seams 31 so that the disengagement force at mesial end is substantially stronger than the distal section disengagement force. Of course, the mesial end separation force remains within that reasonably necessary to completely separate the cover when desired.

Figure 4:
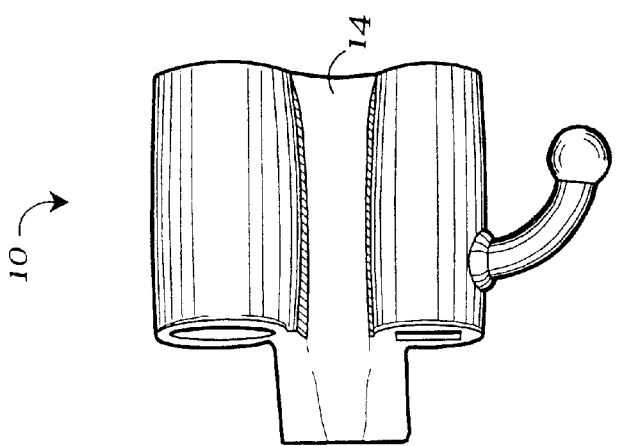
FIG. 4 is a plan view of a buccal tube of the invention with its convertible cap removed.

In operation, wherein it is desired to engage, for example, an adjacent (second) molar, the cap 19 is removed, utilizing an opener tool that shears the integral seams 20. The tool is conventional and may be of the type described in U.S. Pat. No. 4,669,979. FIG. 4 shows the buccal tube 10 with the cover removed, wherein the arch wire slot 14 is open and the tube 10 functions as a conventional bracket with free access to the tie wings 17 for securely ligating the arch wire in place.

The buccal tube of the invention, including its controlled cover integral seams dimensions, is readily manufactured by metal injection molding techniques that permit close tolerances of relatively complex designs.

Figure 5:
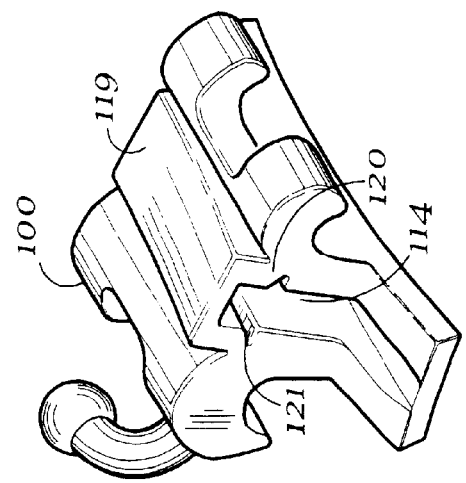
FIG. 5 is a perspective view of another embodiment of the buccal tube of the invention comprising principally a convertible arch wire slot wherein the cover is secured by integral seams.

Referring to FIG. 5, another embodiment 100 of the invention is shown in perspective view. In this embodiment convertible cover 119 covers arch wire slot 114. As in the first embodiment the seams 120 securing the cover to the top of the arch wire slot are integral with the body portion of the tube. Parallel notches 121 are provided that taper in depth mesially-distally to provide a line of separation requiring a substantially greater separation force at the mesial end than the distal end.

Figure 6:
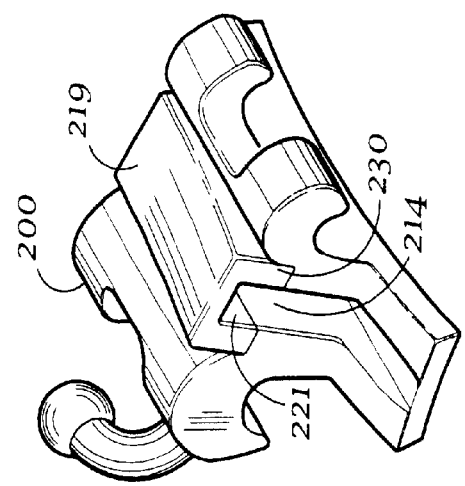
FIG. 6 is yet another embodiment of this invention in perspective view wherein the cover is brazed to an arch wire slot top provided with tapered adhering ledges.

Referring to FIG. 6, yet another embodiment 200 of the convertible buccal tube of the invention is shown in perspective. In the embodiment the convertible cover 219 is brazed to the top of the arch wire slot 214 by soldering, typically with pure silver or other biocompatible solder. The top of the arch wire slot and cap are formed with contact surfaces that taper in surface area from the mesial to the distal end of the buccal tube such that more adhering solder secures the cover in place mesially than distally. Preferably ledges or channels 230 are cut in parallel into the top of the arch wire slot 214 to accommodate securing the cap 219 in position. The cap contact surfaces are tapered to match the arch wire slot ledges which are preferably about 50% wider at the mesial entryway than the distal exit. The cap 219 is also shaped to provide a flared entryway 221 preferred at the mesial end of the buccal.

What is claimed is:

1. A convertible buccal tube, comprising:
   a base attachable to a tooth surface or band on said tooth;
   a body projecting from said base to define a mesially and distally extending arch wire slot; and
   a cover extending over said slot that includes seams connecting said cover and body extending mesially-distally, said seams of a strength selected to facilitate disengaging said cover from the body, said seams being stronger at their mesial portions than their distal portions such that a larger force must be exerted on the mesial portion to initiate disengagement of the cover.

2. The convertible buccal tube of claim 1 wherein said seams are formed integrally with said body.

3. The convertible buccal tubes of claim 2 wherein parallel mesial distal extending notches are formed adjacent said seams, tapering mesially-distally such that about 50% greater force is required to separate said seams at its mesial portion than its distal portion.

4. The convertible buccal tube of claim 1, wherein said mesial portion of said integral seam is 50% stronger than its distal portion.

5. The convertible buccal tube of claim 1, said cover further comprising a flared mesial portion such that the covered arch wire slot has a greater opening at its mesial portion than the distal portion, to facilitate engagement at the tube by an arch wire.

6. The convertible buccal tube of claim 5, wherein said mesial flared portion is about 50% larger in cross sectional area than the distal cross section of the arch wire slot.

7. The convertible buccal tube of claim 5, wherein said mesial flared portion extends about 25% of the length of said arch wire slot.

8. The convertible buccal tube of claim 1, wherein said cover seam mesial portion requires a 15 kg force for initiating removal while said distal seam portion is severable at about 10 kg wherein undesired premature separation of said cover is resisted.

9. A convertible buccal tube, comprising:

a base attachable to a tooth surface or band on said tooth;

a body projecting from said base to define a mesially and distally extending arch wire slot; and a cover, extending mesially-distally substantially covering said arch wire slot, wherein said cover is secured to said body by mesial distal seams, said seams of selected strength to facilitate separating said cover from said body by exerting a desired force on said seam, said cover and seams avoiding premature severance, wherein said mesially-distal seams are stronger at their mesial portions than their distal portions, and wherein said cover is flared at its mesial portion, further limiting premature separating forces being exerted on said cover occasioned by inserting archwires in said tube arch wire slot.

10. The convertible buccal tube of claim 9, wherein said mesial portions of said seams are 50% stronger than their distal portion.

11. The convertible buccal tube of claim 10, wherein said seams are formed by metal injection molding such that the thickness of said seam varies mesially-distally having an increased thickness and strength at its mesial portion.

12. The convertible buccal tube of claim 10, wherein said seam is at least 50% thicker at its mesial portion than it distal portion such that the force required to separate said cover exceeds a desired force.

13. The convertible buccal tube of claim 9, wherein said mesial flared portion is 50% larger in cross sectional area than the distal cross sectional area of said arch wire slot.

14. The convertible buccal tube of claim 9, wherein said strengthened and flared portion of said cover extends about an initial 20–40% of the axial length of said arch wire slot.

15. The convertible buccal tube of claim 9 wherein the cap is adhesively attached to said arch wire slot, said slot including parallel ledges tapered mesially-distally to provide adhering contact surfaces and said cap includes complimentary tapering contact surfaces, such that a substantially greater force is required to separate the cap adhered to the ledges mesially than distally.

16. The convertible buccal tube of claim 15 wherein said adhesive attachment is by brazing and said ledges are about 50% wider at their mesial ends.

* * * * *